US005748492A

United States Patent [19]

Vander Heyden et al.

[11] Patent Number: 5,748,492
[45] Date of Patent: May 5, 1998

[54] MEASURING HEATING VALUE USING CATALYTIC COMBUSTION

[75] Inventors: William H. Vander Heyden, Mequon, Wis.; Ronald Arthur Berg, Tulsa, Okla.

[73] Assignee: Badger Meter, Inc., Milwaukee, Wis.

[21] Appl. No.: 599,003

[22] Filed: Feb. 9, 1996

Related U.S. Application Data

[63] Continuation-in-part of Ser. No. 449,506, May 24, 1995, abandoned.

[51] Int. Cl.$^6$ ................................................. G01N 11/02
[52] U.S. Cl. .............................................. 364/499; 73/23.31
[58] Field of Search ............................... 364/499, 496, 364/497, 500, 510, 550, 557; 73/23.2, 23.31, 25.01, 25.03, 861.01, 861.02, 861.03, 196, 199; 436/147, 2, 159; 422/51, 94, 95, 96, 98; 374/31, 36, 37, 40, 33

[56] References Cited

U.S. PATENT DOCUMENTS

| | | | |
|---|---|---|---|
| 3,777,562 | 12/1973 | Clingman, Jr. | 73/190 |
| 4,062,236 | 12/1977 | Clingman, Jr. | 73/190 |
| 4,125,018 | 11/1978 | Clingman, Jr. | 73/190 |
| 4,125,123 | 11/1978 | Clingman, Jr. | 137/80 |
| 4,285,245 | 8/1981 | Kennedy | 73/861 |
| 4,329,873 | 5/1982 | Maeda | 73/190 CV |
| 4,614,721 | 9/1986 | Goldberg | 436/147 |
| 5,012,432 | 4/1991 | Stetter et al. | 364/557 |

FOREIGN PATENT DOCUMENTS 0 304 266  8/1988  European Pat. Off. .

*Primary Examiner*—Emanuel T. Voeltz
*Assistant Examiner*—M. Kemper
*Attorney, Agent, or Firm*—Quarles & Brady

[57] ABSTRACT

The heating value of a sample gas is calculated by a microcontroller (12) from the heating value of a reference gas, and from flow ratios determined as the gas is consumed by catalytic combustion. In a preferred embodiment, chambers (5, 14) of fixed volume are charged to a predetermined pressure with a reference gas and a sample gas, respectively, and flowed to the catalyst at variable, changing flow rates as pressure decays. During the discharge cycle, a pressure transducer (13) senses the decaying pressure and this information is input to the microcontroller (12), which computes molar flow rates and which also senses the power level of combustion through a bridge circuit (24) in the catalytic apparatus (8, 10). Based on a ratio of molar flow rates and a ratio of corresponding power levels, a heating value of the sample gas is calculated by the microcontroller (12) and output to a visual display or other output device.

16 Claims, 3 Drawing Sheets

MEASURING HEATING VALUE USING CATALYTIC COMBUSTION

This application is a continuation-in-part of application Ser. No. 08/449,506 now abandoned.

BACKGROUND OF THE INVENTION

The field of the invention is methods and apparatus for determining the heating value of gases. The measurement of the heating value of natural gas is important in the distribution and sale of natural gas. There are three commonly used methods for measuring heating value.

One method is stoichiometry, in which combustion is substantially complete. This type of combustion produces maximum flame temperature and minimum oxygen in the exhaust stream. In this case, natural gases are combusted with air and the fuel-to-air ratio is adjusted until combustion results in either a maximum flame temperature or the stoichiometric point of perfect combustion, i.e., the knife edge when there is no remaining oxygen.

Clingman, U.S. Pat. No. 3,777,562, is an example of this method. In Clingman, heating value is measured by combustion of a gas with amounts of air that are adjusted to obtain the maximum flame temperature. This is further disclosed in Clingman, U.S. Pat. Nos. 4,062,236, 4,125,018 and 4,125,123. In each of these patents, the combustion of the air-gas mixture is accomplished with a combustion flame on a burner top and with a temperature sensing device such as a thermocouple.

A second method for measuring heating value is constituent analysis. Using a chromatograph, the fraction of each chemical constituent in the gas is determined. Then, the heating value is determined by summing the heating value for the individual constituents.

The third method is calorimetric measurement in which a volume of the gas is sampled and then completely combusted. The combustion may be by flame or by other methods not producing an open flame, such as by passing the gas over a catalytic material. In the case of catalytic combustion, the amount of heat liberated can be measured either by temperature changes related to the catalytic reaction, by changes in power supplied to heat the catalyst or by measuring the temperature of the catalytic material.

Catalytic combustion occurs at temperatures below a normal ignition temperature associated with hydrocarbons. For example, methane when mixed with air, in a stoichiometric proportion, will ignite at a temperature of about 630° C. and reach an open flame temperature exceeding 1600° C. Catalytic oxidation can take place at catalyst temperatures as low as 400° C. although efficient catalysis is then achieved at a temperature near 500° C. Therefore, for methane-containing gaseous mixtures, catalytic oxidation is enabled below the ignition temperatures of the surrounding atmosphere.

In catalytic combustion practice, it is usual to mix the sample gas with a fixed amount of air, usually excess air, where the proportion of air is more than sufficient to provide all the oxygen required for oxidation of the sample gas. In catalytic oxidation, the temperature of the catalyst must be limited to prevent overheating and runaway temperature and reaction conditions.

Goldberg, U.S. Pat. No. 4,614,721 and Stetter, U.S. Pat. No. 5,012,432, describe measurement of heating values using catalytic combustion. In Goldberg, the measurement of heating value requires measuring temperature before and after catalytic combustion to determine the heating value per unit volume of the gas.

In Stetter, precise constant volumes of the gas are sampled and then oxidized using reaction with a catalyst to generate a signal representative of the heat released. A baseline signal is produced for air, and then a reference gas flow and a sample gas flow are reacted with the catalyst to provide further signals for comparison with the baseline signal.

In previous catalytic heating value measurements, extreme stability of gas and air volumes was required to achieve accuracy. The prior art utilizes means for holding gas flow rates constant and means for holding fixed gas volumes. This present invention provides improved methods and apparatus for measuring heating values in a catalytic combustion apparatus using variable flow rates.

SUMMARY OF THE INVENTION

The present invention measures the heating value of a gas using flameless catalytic combustion and improved flow rate measuring apparatus.

The invention establishes a variable fuel mixture within a general range and measures the gas combustion power introduced into the catalytic reactor and the associated molar flow rate of the gas. A reference gas and the sample gas are measured in respective cycles. The only requirement is that the molar flow rate of the gas be compared with its associated combustion power levels supporting the catalytic combustion.

In the present invention, an air flow is established which is well in excess of the air required to combust the gas. A reference gas is mixed with the air, and the gas flow rate is allowed to change slowly with time in an uncontrolled fashion. The gas/air flow is directed over or through a catalytic bed or bead, where a portion of the fuel is oxidized. The power level supporting combustion varies with the gas flow rate. At a selected combustion power level, the molar flow rate of the gas is measured by appropriate sensors.

This cycle is followed by introduction of a flow of the sample gas which passes through the same catalytic cycle and which varies with time. When the combustion power level at the catalyst reaches a selected power level, the molar flow rate of the sample gas is measured.

It will be shown that the heating value of the sample gas can be calculated from the ratio of the molar flow rates of the sample gas and the reference gas, the ratio of the combustion power levels of the sample gas and the reference gas, and a known heating value for the reference gas.

In the preferred embodiment, the fuel-to-air mixture is varied by allowing pressure in a volume chamber to decay to produce a decreasing flow of fuel which progressively changes the fuel-to-air mixture. Molar flow rates are measured for a sample gas and a reference gas within the cycle of catalytic combustion. Heating value for a sample gas can then be calculated with a pre-stored value for the heating value of the reference gas.

Various objects and advantages will be apparent to those of ordinary skill in the art from the description of the preferred embodiment which follows. In the description, reference is made to the accompanying drawings, which form a part hereof, and which illustrate examples of the invention. Such examples, however, are not exhaustive of the various embodiments of the invention, and, therefore, reference is made to the claims which follow the description for determining the scope of the invention.

DETAILED DESCRIPTION OF THE PREFERRED EMBODIMENT OF THE INVENTION

Figure 1:
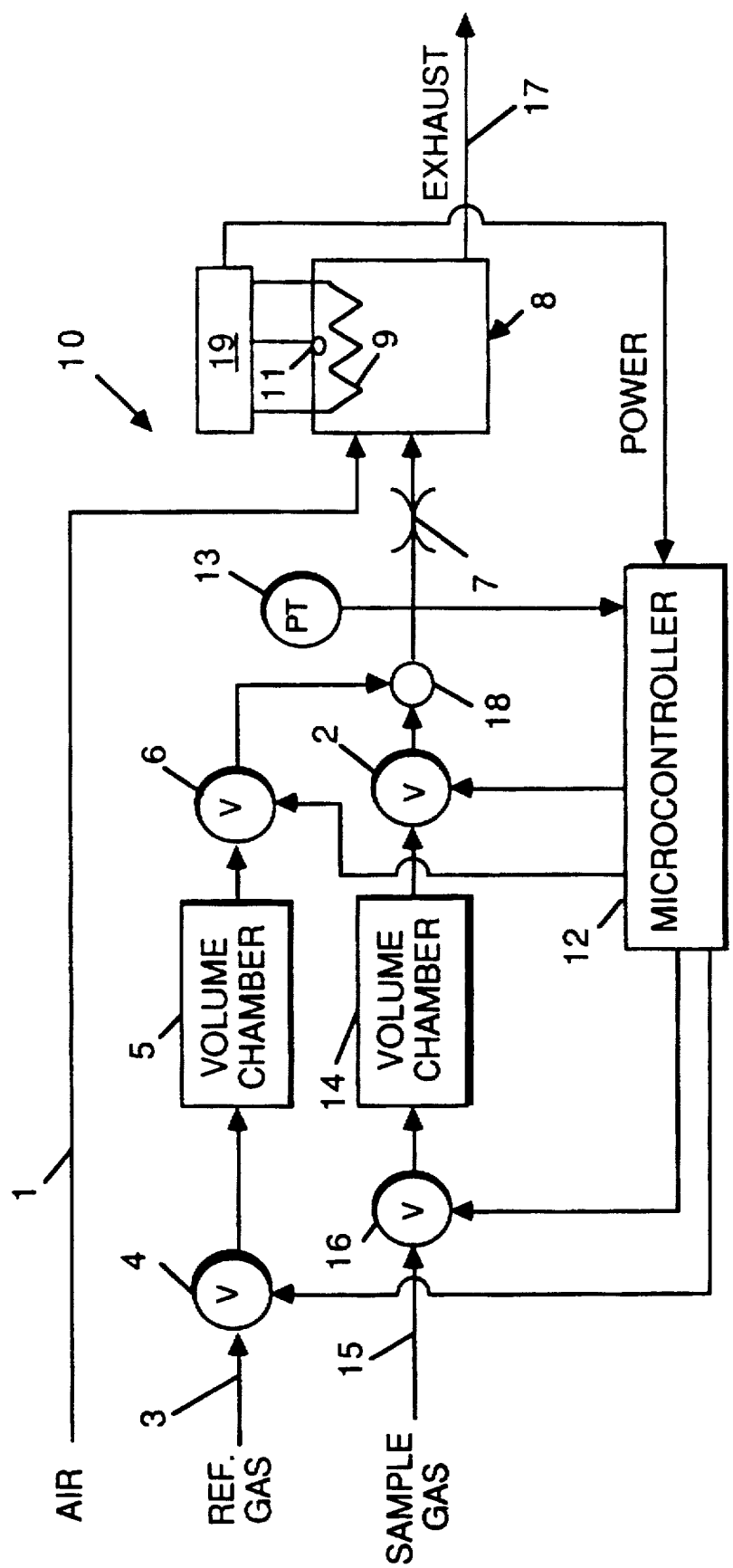
FIG. 1 is a block diagram of an apparatus for practicing the method of the present invention.

Referring to FIG. 1, the apparatus 10 of the present invention includes a line 1 for supplying air from an external air supply (not shown) to a catalytic apparatus 8. The flow rate of the air to catalytic apparatus 8 is not critical and can vary by 10% in a slow fashion, but must always be in excess of combustion requirements.

The catalytic apparatus 8 includes a bed that is composed of material, such as platinum and/or palladium coated on a fibrous material, which promotes and enhances oxidation of the gas without flame combustion. The apparatus further includes heating element 9, which is located at, or in, the catalytic bed to provide an initial starting temperature for the reaction. The heating element 9 will heat the catalytic material to a temperature of 400° C. or more.

The apparatus 8 also includes a temperature sensor 11 that provides a signal proportional to the temperature at the reaction surface of the catalytic material. Heating element 9 receives electrical power from power source 19. Temperature sensor 11 is embedded in the catalytic material to sense the temperature at the reaction surface of the catalytic material. Temperature sensor 11 generates a signal as an input to power source 19. This signal is recognized by the power source 19 as representative of catalytic temperature.

Figure 2:
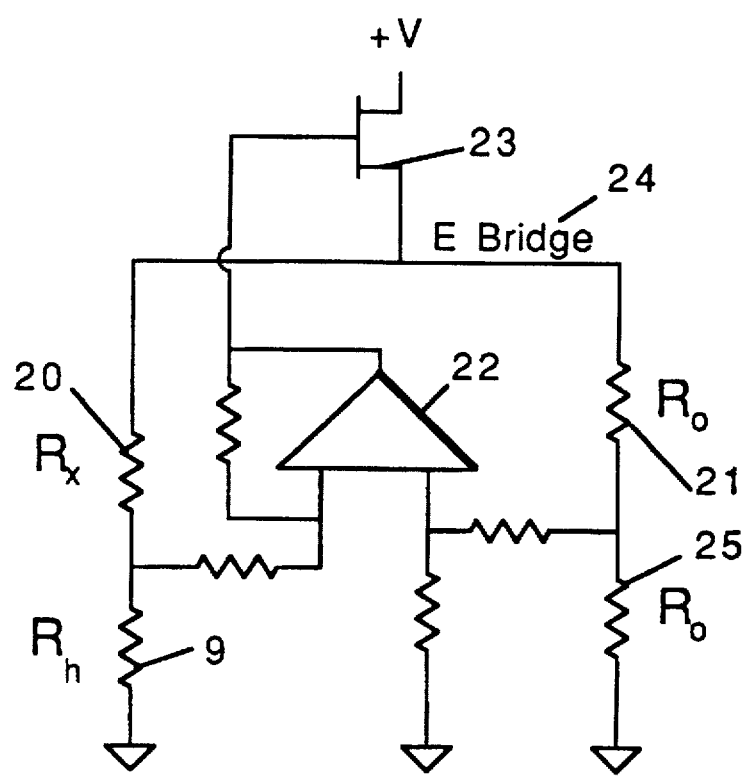
FIG. 2 is a detail schematic diagram of an electrical circuit in the catalytic apparatus of FIG. 1.

FIG. 2 shows details of the catalytic apparatus 8 and power source 10 described above in relation to FIG. 1.

Within elements 8, 19, a bridge circuit 24 as seen in FIG. 2 is formed. On the left side of the bridge resistors 9 and 20 are connected in series. Resistor 9 ($R_h$), also referred to as the heating element 9 in FIG. 1, is typically a platinum coiled-wire resistor. Platinum is selected due to its stable temperature coefficient over a wide temperature range. Its resistance value ($R_h$) is a function of temperature $R_h = R_{hO}(1+\alpha\Delta T)$. Resistor 9 also acts as the temperature sensor 11 of the catalyst. Resistor 20 is a resistor whose value ($R_x$) is selected to be the desired resistance of 9 at the temperature selected for the operation of the catalyst.

On the right side of the bridge 24, resistors 21, 25 are connected in series to divide the applied voltage (+V). In FIG. 2, the resistors are shown of equal value ($R_0$), but that is not a strict requirement.

Operational amplifier 22 senses the difference between the center tap voltages on the right and left sides of the bridge 24 and amplifies that difference. The result is applied to power FET 23 to change the voltage on the bridge 24 until the center tap voltages of the two sections become equal.

Therefore, the electrical power level into the heater/sensor 9 is that required to hold the resistance and temperature of heater/sensor 9 constant. If gas combustion takes place, the gas power introduced to the catalyst associated with heater/ sensor 9 will attempt to raise the heater/sensor temperature and the applied electrical power will reduce in proportion to maintain the heater sensor temperature constant.

An exhaust stream 17 (FIG. 1) is exhausted from catalytic device 8. This exhaust stream 17 includes air, the products of combustion and any unburned gas. Additional steps may be taken to process the exhaust stream.

Microcontroller 12 (FIG. 1) is a suitable microelectronic CPU (central processing unit) with A-to-D and D-to-A interface circuitry. Microcontroller 12 operates by executing program instructions, some of which are represented by blocks in the flow chart in FIG. 4, the instructions being stored in a memory also represented generally by reference 12.

Microcontroller 12 senses the power level of combustion through an input connected to power source 19. Microcontroller 12 also controls the flow of reference gas and sample gas to the catalytic apparatus in successive cycles by operating a series of valves and chambers.

In one cycle, a reference gas flows through on-off valve 4 into volume chamber 5, and later through on-off valve 6 to a junction 18 leading to flow restrictor 7 and finally, to the catalytic apparatus 8. The actual rate of flow is solely determined by the pressure in volume chamber 5 and the flow properties of flow restrictor 7. It is an objective of this invention to utilize uncontrolled gas flow rates but introducing controlled flow rates would serve the same purpose with more complication.

Control valve 4 is opened to fill the volume chamber 5 with reference gas from sample gas source 3. Flow into volume chamber 5 increases pressure in volume chamber 5 to reach a pre-determined, but non-critical pressure usually determined by the pressure in supply line 3, and then inlet flow control valve 4 is closed. After closing valve 4, microcontroller 12 opens control valve 6 to establish flow of reference gas through junction 18 and restrictor 7 to catalytic apparatus 8 where a portion of the reference gas is combusted.

In another cycle, a sample gas flows through on-off valve 16 into volume chamber 14, and later through on-off valve 2 to junction 18 leading to flow restrictor 7 and finally, to the catalytic apparatus 8.

Control valve 16 is opened to fill the volume chamber 14 with sample gas from sample source 15. Flow into volume chamber 14 increases pressure in volume chamber 14 until a pre-determined, but non-critical pressure usually determined by the pressure in supply line 15, then inlet flow control valve 16 is closed. After closing valve 16, microcontroller 12 opens control valve 2 to establish flow of sample gas through restrictor 7 and on catalytic bed 8 where a portion of the sample gas is combusted as was done with the reference gas.

As each cycle progresses, gas trapped in volume chamber 5 or 14 is withdrawn and the pressure in volume chamber 5 or 14 reduces. Microprocessor unit 12 monitors the changes in pressure in volume chamber 5 or 14 using pressure transducer 13 to determine molar flow rate. It should be noted that measurement of molar flow rate using the rate of change of pressure in volume chamber 5 or 14 is of the type disclosed in Kennedy, U.S. Pat. No. 4,285,245 for sensing molar flow rate in response to pressure changes due to flow of gas out of a chamber. This eliminates the molecular weight of the gas from consideration in gas measurements. Such a flow meter is incorporated in a product commercially offered by the assignee under the trade designation "TRU-THERM".

Besides measuring molar flow rate, microcontroller 12 also monitors the power level required for catalytic oxidation of the sample gas or reference gas. In the preferred embodiment, power source 19 continuously adjusts power to heater 9 maintaining a constant temperature on sensor 11. As the gas flow rate changes, power changes to heater 9 represent the power of gas combustion on the catalytic bed 8. These power levels are sensed by the microcontroller 12. At a predetermined combustion power level or change in combustion power level, the molar flow rate from volume chamber 14 is calculated and stored by microcontroller 12.

The use of two volume chambers, 5 and 14, is not required but is the preferred embodiment. Using one chamber slows the measurement process because a single chamber utilizing two gases has the problem of residual gas residency and several cycles of exhaust are required to completely exchange the gas. If speed of response is not the overriding objective, the measurement can be modified to use reference gas only infrequently and a single volume chamber can be used.

Figure 3:
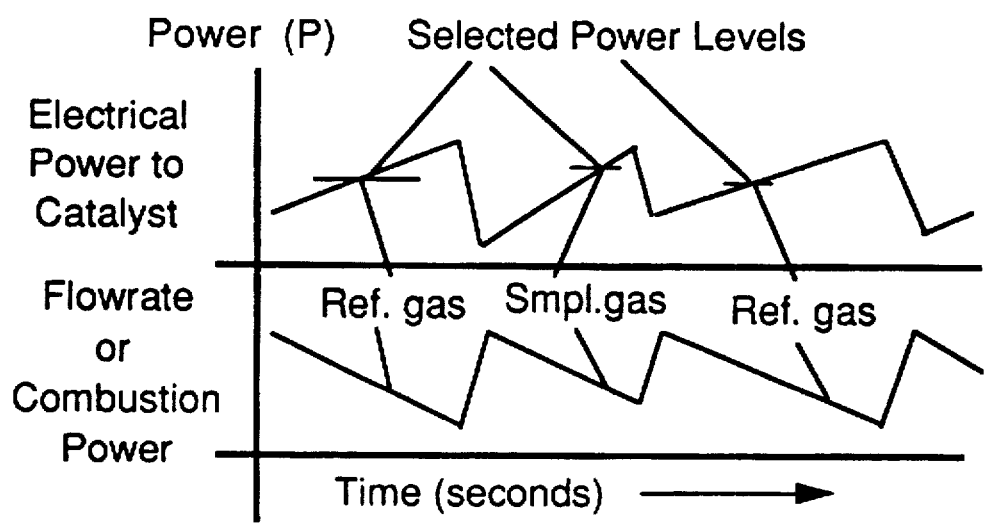
FIG. 3 is a graph of power versus time illustrating operation of the apparatus of FIG. 1.

The sample gas and reference gas are alternately cycled through the catalytic bed. In FIG. 3, the first cycle is a reference gas cycle and the flow of reference gas changes over a period of 10 to 20 seconds. When the pressure of the reference gas reaches a low point, the switch is made to sample gas and the decay cycle of the sample gas begins. This is a repeating sequence. The method is carried out at ambient temperatures of from approximately −40° F. to 130° F.

As the gas flow rate decays, the amount of combustion power level changes as well, and the electrical power to the heater/sensor in the catalyst rises in inverse proportion to the flow rate. In each flow cycle, there is a selected power level for which the molar flow rate is measured and this value is used to compute the power level ratio "$\eta$" as well as the heating value of the sample gas.

The molar heating value $H_m$ is defined as the amount of heat which can be liberated by combustion of a mole of the gas and has typical units of energy/mole. If the molar flow rate of a gas, $n_g$, with units of moles/second, is multiplied by molar heating value, the result is the power of combustion described as $\Delta P = H_m \dot{n}_g$. If the combustion power of the sample gas and reference gas are identical at the selected point of measurement, then equating the two combustion powers results in:

$$H_{ms} = H_{mr} \left( \frac{\dot{n}_r}{\dot{n}_s} \right) \quad (1)$$

where the subscripts r and s refer to reference and sample conditions.

A desirable feature of this invention is that speed of response can be improved by terminating the individual measurement cycles prior to completion. If the change in combustion powers of the reference and sample cycle are not equal but are in a known ratio, then Eq. (1) can be modified introducing a correction factor, $\eta$, which is the ratio of the changes in power levels and (1) is restated as:

$$H_{ms} = \eta H_{mr} \left( \frac{\dot{n}_r}{\dot{n}_s} \right) \quad (2)$$

where $\eta$ is the ratio of the two power levels. It should be clear that $\eta$ can take on values, in the extreme, between zero and unity.

A mole of gas contains a fixed number of molecules, known as Avogadro's number, and occupies a defined volume Vm which is a function of temperature and pressure. At 0° C. and 14.696 psia, this volume, for an ideal gas is 22.4138 liters. The effect of compressibility must be recognized and used to define the molar volume of a real gas as $V_{m\,real} = V_{m\,ideal} Z_{real}$, with units of volume per mole and where the compressibility, $Z_{real}$, is calculated at the temperature and pressure of the measurement. Therefore the volume heating value (energy/volume) of the gas is:

$$H_{vs} = \frac{\eta H_{mr} \left( \frac{\dot{n}_r}{\dot{n}_s} \right)}{V_{m\,ideal} Z_{real}} \quad (3)$$

The heating value as defined in equation (3) will be stated at a standard temperature and pressure and a user will select the standard values. This can be easily accommodated using the general gas law and is known to anyone familiar with the art of gas computation.

Sensing the molar flow rate of the gas flowing from volume chambers 5 or 14 is accomplished by measuring the rate of change or change of pressure as the gas in the volume is withdrawn. The relation between the molar flow rate of the gas and the rate of change of pressure is obtained from the general gas law and is:

$$\dot{n} = \frac{\dot{P}V}{Z^2 RT} \quad (4)$$

where $\dot{n}$ is the molar flow rate and $\dot{P}$ is the rate of change of pressure.

Figure 4:
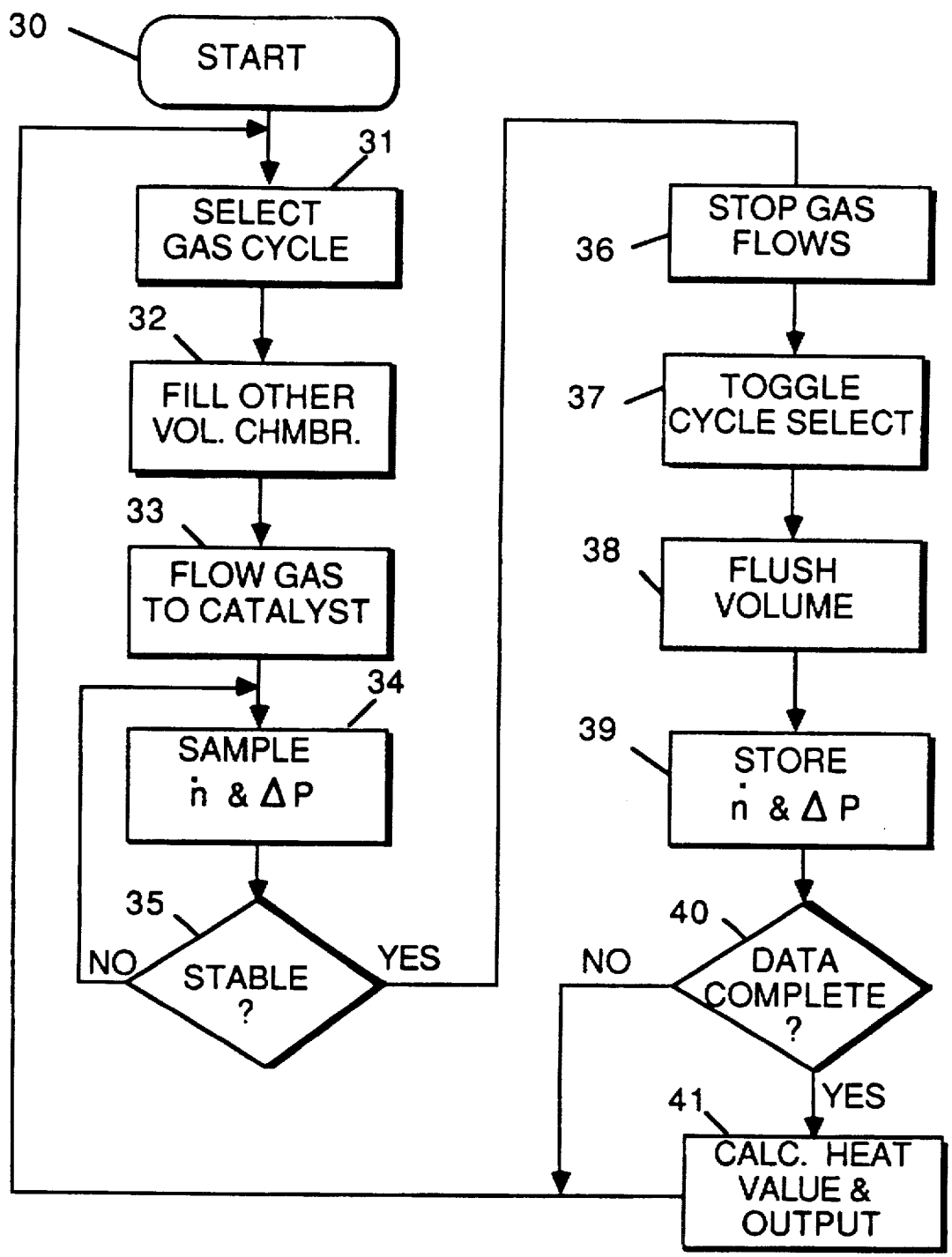
FIG. 4 is a flow chart of the operation of a microcontroller in the apparatus of FIG. 1.

FIG. 4 shows the operation from the viewpoint of the microcontroller 12 in executing its control program. The start of the operation is represented by start block 30. The microcontroller 12 executes instructions to select either the reference gas cycle or the sample gas cycle, as represented by process block 31. If the reference gas cycle is selected, the microcontroller 12 executes further instructions, represented by process block 32, to open valve 16 and allow sample gas to fill volume chamber 14 in preparation for the next cycle using the sample gas. Next, as represented by process block 33, the microcontroller 12 executes further instructions to open valve 6 and allow reference gas to flow to the catalytic device 8. The microcontroller 12 then executes instructions represented by process block 34 to begin to sample molar flow rate ($\dot{n}$) and the changes in the electrical power ($\Delta P$) required by the catalytic device 8. The microcontroller 12 executes instructions represented by decision block 35 to see if the molar flow rate and electrical power requirements have stabilized. If the result in "NO," it loops back to continue with another sample. If the result is "YES," it proceeds to execute instructions represented by block 36 to end the first cycle and prepare for the next cycle.

As represented by process block 36, microcontroller 12 executes instructions to stop the gas flow of the reference gas by closing valve 6. The microcontroller 12 then executes instructions represented by process block 37 to change the selection to the other gas cycle. The microcontroller 12 then executes instructions represented by process block 38 to flush chamber 5. Next, the microcontroller 12 then executes instructions represented by process block 38 to store the final flow rate and power values for the cycle just completed. A check is them made, as represented by decision block 40, to see if both a reference cycle and a sample gas cycle have been completed within a recent time period. If the result is "YES," the data can be used calculate heating value as represented by process block 41. The heating value is then output to a visual display (not shown in FIG. 1) or another type of output device. If the data is not complete, the result from decision block 40 is "NO," and program returns to start a new gas measurement cycle at block 31.

This has been a description of examples of how the invention can be carried out. Those of ordinary skill in the art will recognize that various details may be modified in arriving at other detailed embodiments, and these embodiments will come within the scope of the invention.

Therefore, to apprise the public of the scope of the invention and the embodiments covered by the invention, the following claims are made.

We claim:

1. A method of measuring heating value of a combustible gas, wherein a reference gas and a sample gas are brought into contact with a catalyst in separate cycles to cause flameless oxidation of the reference gas and the sample gas, respectively;

wherein a power level and a corresponding value for flow rate of the sample gas are detected;

said method further comprising:

varying a flow rate for the reference gas to the catalyst to obtain a changing power level for the catalyst;

detecting the flow rate of the reference gas at a selected power level more than a maximum electrical power supplied to the catalyst;

varying a flow rate for the sample gas to the catalyst to obtain a power level either equal to or proportional to the selected electrical power level for the reference gas;

detecting said flow rate for the sample gas at said power level at which the flow rate was detected for the reference gas; and calculating the heating value of the sample gas in response to a ratio of reference gas flow rate and sample gas flow rate relative to the selected electrical power level.

2. The method of claim 1, wherein the heating value of the sample gas is calculated in response to a ratio of a power level corresponding to the reference gas flow rate and a power level corresponding to the sample gas flow rate.

3. The method of claim 1, wherein the flow rates of the sample gas and the reference gas are molar flow rates.

4. The method of claim 1, wherein the flow rate of the sample gas is varied by releasing a volume of gas from a pressurized chamber and allowing pressure in the chamber to decrease.

5. The method of claim 1, wherein the flow rate of the reference gas is varied by releasing a volume of pressurized gas from a first chamber and allowing pressure in a first chamber to decrease.

6. The method of claim 5, further comprising filling and pressurizing a second chamber with sample gas as the reference gas is being released from said first chamber.

7. The method of claim 1, further comprising sensing the power level from the catalyst for the reference gas and the sample gas to obtain a power level of equal value corresponding to respective flow rates for the reference gas and the sample gas.

8. The method of claim 1, wherein said method is carried out at ambient temperatures of from approximately −40° F. to 130° F.

9. The method of claim 1, further comprising sensing the temperature of catalytic oxidation of said reference gas and said sample gas and in response thereto controlling power levels to the catalyst to control the temperature of catalytic oxidation of said reference gas and said sample gas.

10. The method of claim 1, wherein the steps of flowing, varying the flow rate and detecting the flow rate of the reference gas are carried out in a first cycle, which is then followed by a second cycle including the steps of flowing, varying the flow rate and detecting the flow rate of the sample gas.

11. An apparatus for determining the heating value of a combustible gas, the apparatus comprising:

means for establishing a variable flow rate of a reference gas that flows into contact with a catalyst under conditions of changing pressure;

means for establishing a variable flow rate of a sample gas that flows into contact with the catalyst under conditions of changing pressure;

means for detecting levels of electrical power supplied to the catalyst for catalytic combustion of the reference gas and the sample gas;

means for detecting the flow rates of the reference gas and the sample gas corresponding to selected levels of electrical power supplied to the catalyst for catalytic combustion of the reference gas and the sample gas, respectively; and means for calculating the heating value of the sample gas in response to detection of the flow rates of the reference gas and the sample gas at selected levels of electrical power supplied to the catalytic heater for catalytic combustion of the reference gas and the sample gas respectively.

12. The apparatus of claim 11, wherein said means for establishing a variable flow rate of a reference gas includes a first chamber of fixed volume, a first valve controlling the flow of reference gas into said first chamber, a second valve controlling the flow of reference gas out of said first chamber, and means for controlling the operation of the first valve and the second valve.

13. The apparatus of claim 12, wherein said means for establishing a variable flow rate of a sample gas includes a second chamber of fixed volume, a third valve controlling the flow of reference gas into said second chamber, a fourth valve controlling the flow of reference gas out of said second chamber, and means for controlling the operation of the third valve and the fourth valve.

14. The apparatus of claim 13, wherein said means for detecting the flow rates of the reference gas and the sample gas includes a pressure transducer for detecting the decrease of pressure in said first chamber and said second chamber, and calculating means for calculating such decrease as a function of time to determine the molar flow rates of the reference gas and the sample gas.

15. The apparatus of claim 11, wherein the means for detecting the level of electrical power supplied to a catalytic heater further comprises a resistance bridge circuit including the catalytic heating element and further comprises a means for sensing electrical power supplied to the catalytic heating element in said bridge circuit.

16. The apparatus of claim 11, wherein said means for calculating the heating value of the sample gas in response to detection of the flow rates of the reference gas and the sample gas and in response to the detection of electrical power supplied to the catalytic heater includes a microelectronic processor which is programmed to carry out said calculations for heating value of the sample gas.

* * * * *

UNITED STATES PATENT AND TRADEMARK OFFICE
CERTIFICATE OF CORRECTION

Patent No.    : 5,748,492

Dated         : May 5, 1998

Inventor(s)   : William H. Vander Heyden, et al.

It is certified that error appears in the above-identified patent and that said Letters Patent is hereby corrected as shown below:

Column 3, line 15, "10" should be --±10%--.

Column 6, line 54, "them" should be --then--.

Column 6, line 57, "used calculate" should be --used to calculate--.

Column 7, line 18, "maximum" should be --minimum--.

Signed and Sealed this

Third Day of November, 1998

*Attest:*

BRUCE LEHMAN

*Attesting Officer*    *Commissioner of Patents and Trademarks*